United States Patent
Wolf et al.

[11] Patent Number: 6,022,358
[45] Date of Patent: *Feb. 8, 2000

[54] DEFORMABLE INTRAOCULAR LENS INJECTING DEVICE

[75] Inventors: John R. Wolf, San Moreno; Vladimir Feingold, Laguna Niguel, both of Calif.

[73] Assignee: Staar Surgical Company, Inc., Monrovia, Calif.

[*] Notice: This patent is subject to a terminal disclaimer.

[21] Appl. No.: 08/766,022

[22] Filed: Dec. 13, 1996

Related U.S. Application Data

[60] Division of application No. 08/403,530, Mar. 14, 1995, abandoned, which is a continuation-in-part of application No. 08/221,013, Apr. 1, 1994, Pat. No. 5,494,484, which is a continuation of application No. 07/953,251, Sep. 30, 1992, abandoned.

[51] Int. Cl.⁷ ....................................................... A61F 9/00
[52] U.S. Cl. ............................................................. 606/107
[58] Field of Search ................................. 606/107; 623/6

[56] References Cited

U.S. PATENT DOCUMENTS

| | | | |
|---|---|---|---|
| 4,597,753 | 7/1986 | Turley | 623/6 |
| 4,681,102 | 7/1987 | Bartell | 623/6 |
| 4,934,363 | 6/1990 | Smith et al. | 606/107 |
| 5,176,686 | 1/1993 | Poley | 606/107 |
| 5,190,552 | 3/1993 | Kelman | 606/107 |
| 5,304,182 | 4/1994 | Rheinish et al. | 606/107 |
| 5,494,484 | 2/1996 | Feingold | 606/107 |
| 5,499,987 | 3/1996 | Feingold | 606/107 |
| 5,571,113 | 11/1996 | McDonald | 606/107 |
| 5,582,614 | 12/1996 | Feingold | 606/107 |

*Primary Examiner*—Richard J. Apley
*Assistant Examiner*—Justine R. Yu
*Attorney, Agent, or Firm*—Klima & Pezzlo, PC

[57] ABSTRACT

A surgical implantation device for insertion of a deformable intraocular lens into the eye through a relatively small incision made in the ocular tissue comprising a lens injecting device having a plunger with a plunger tip configured to provide a side clearance between the plunger tip and lens insertion passageway through the surgical implantation device to accommodate the trailing haptic of the deformable intraocular lens to prevent damage thereto during insertion.

16 Claims, 10 Drawing Sheets

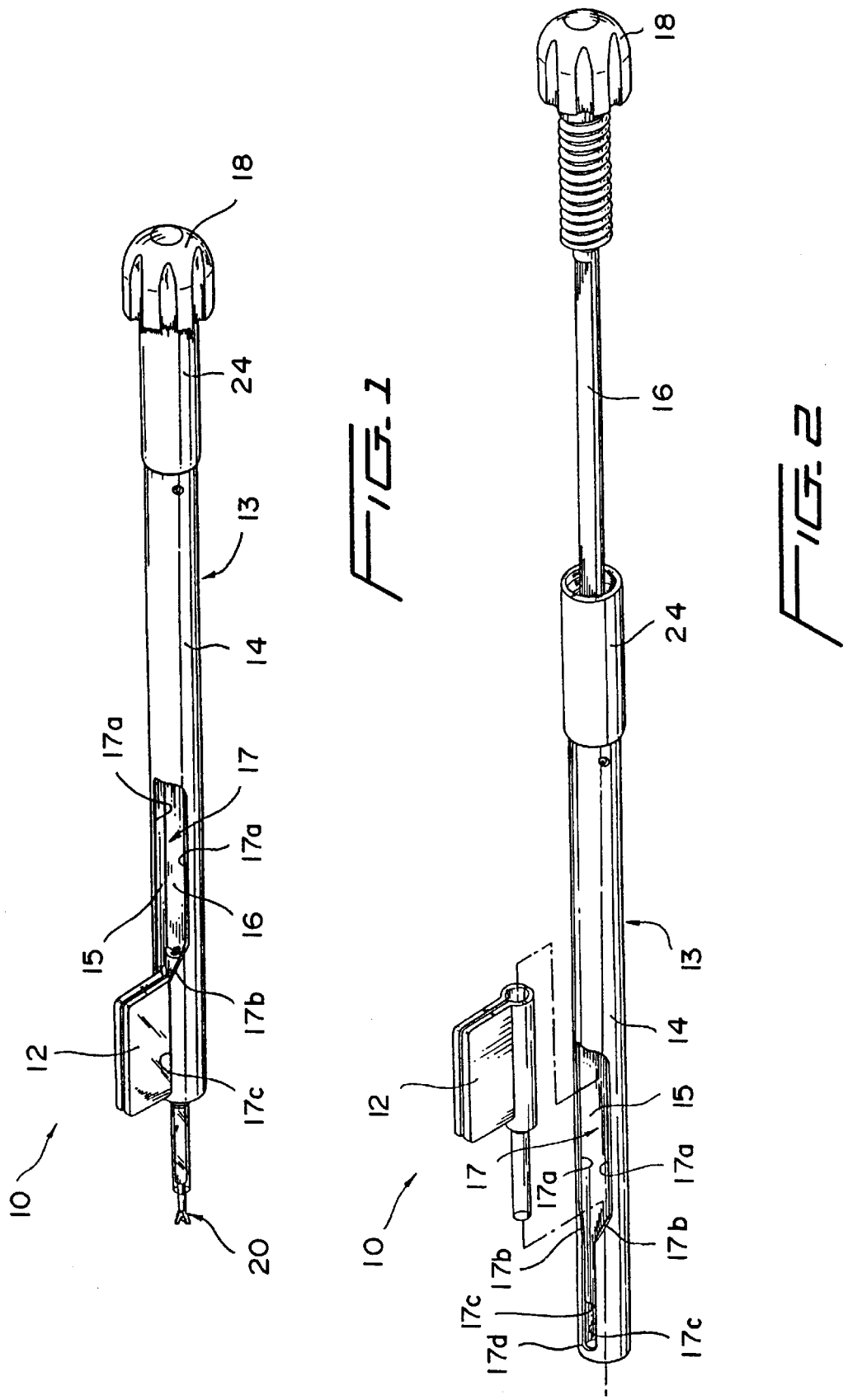

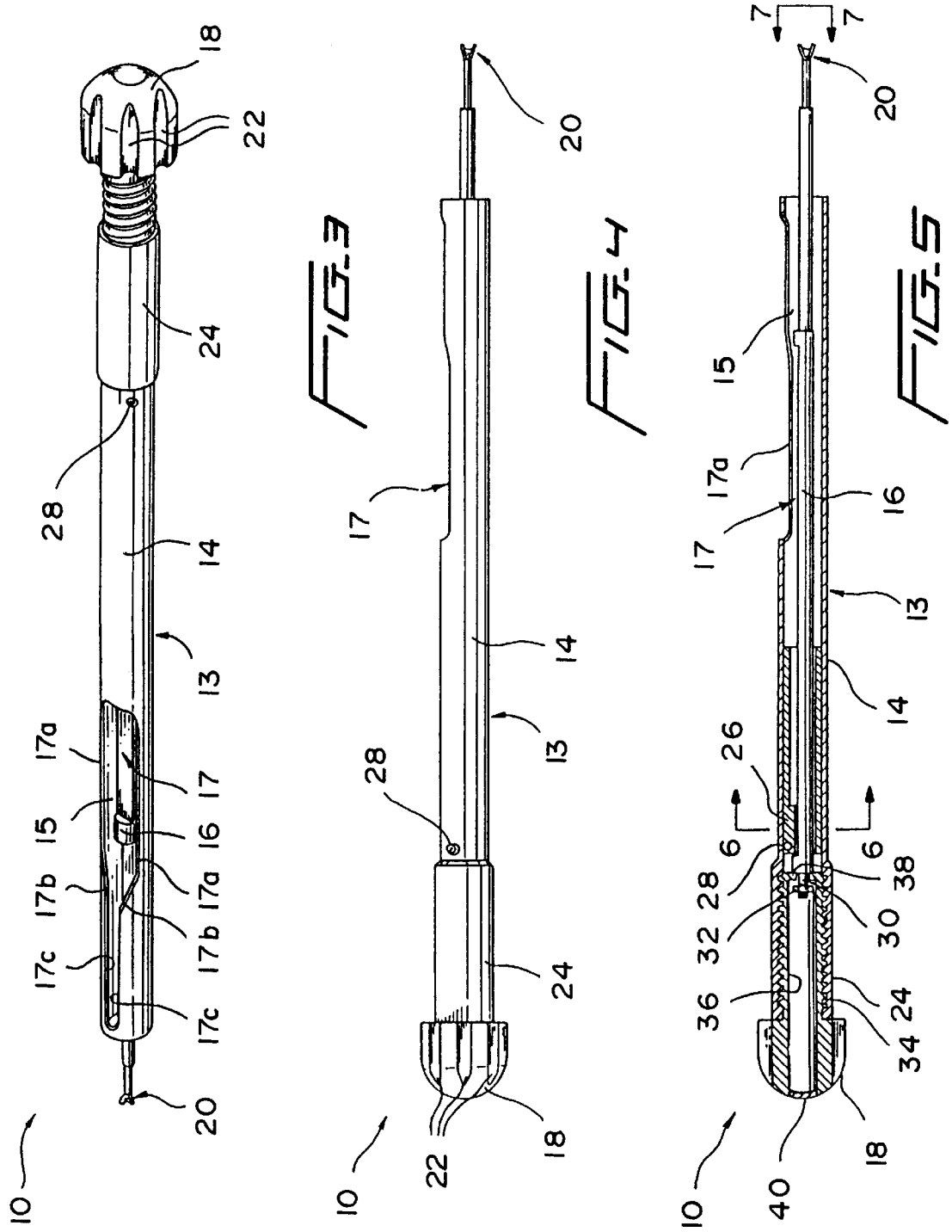

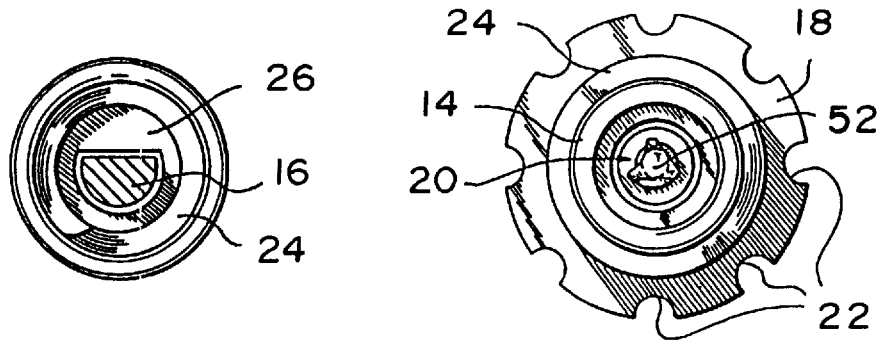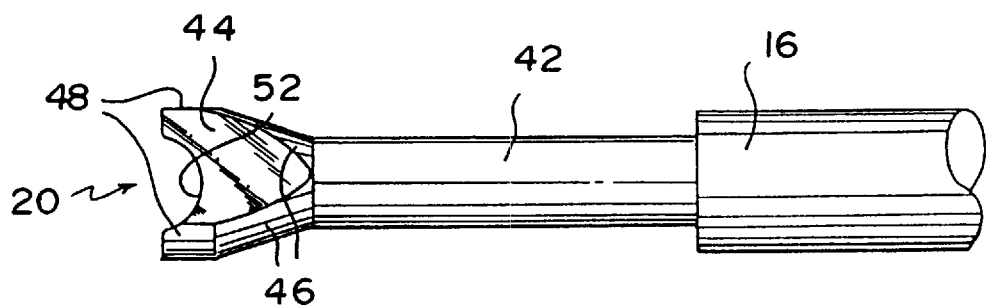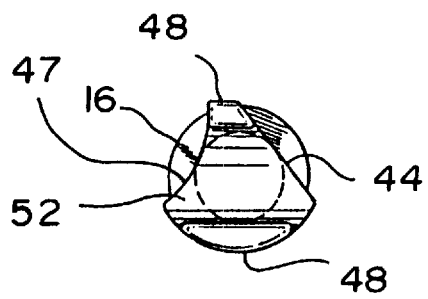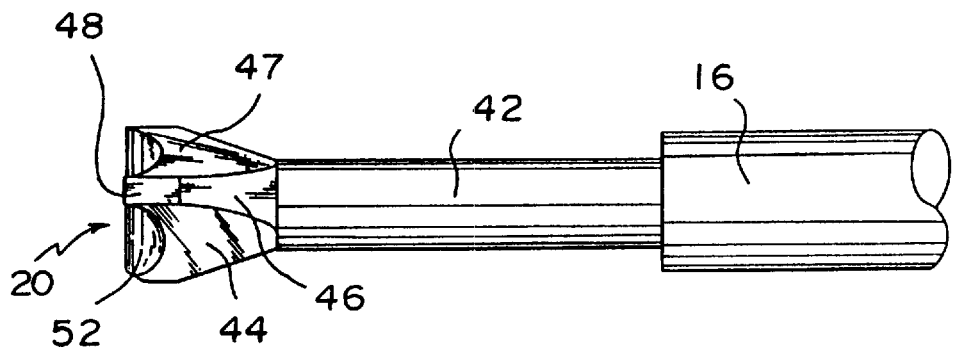

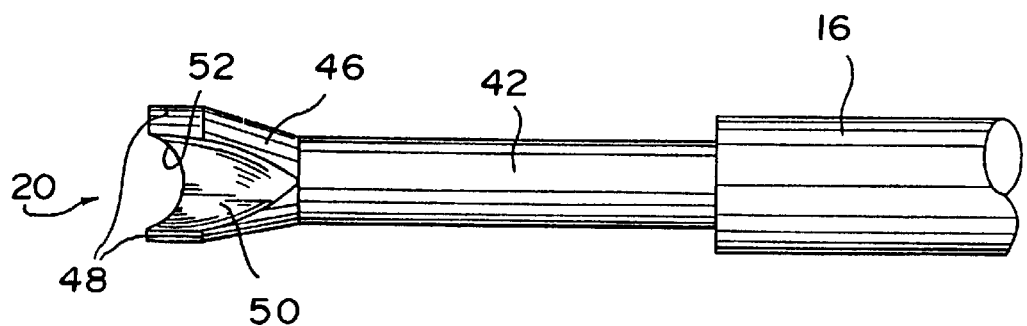
FIG. 11
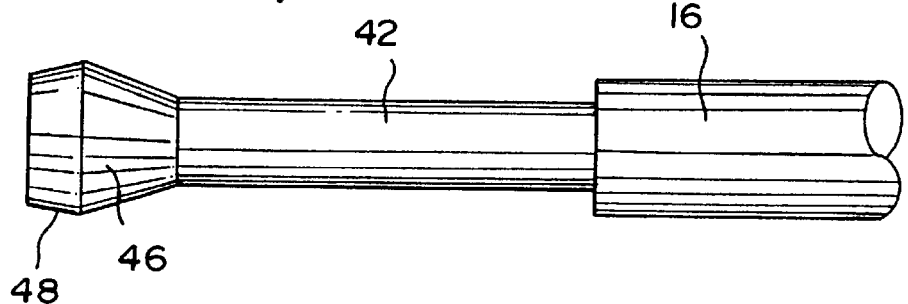
FIG. 12
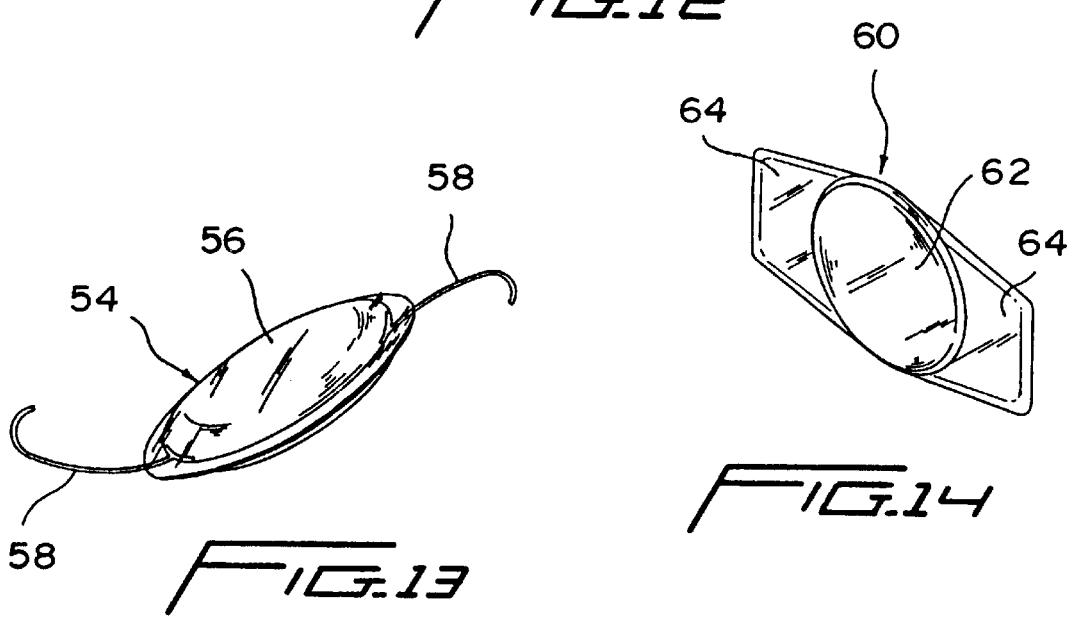
FIG. 13
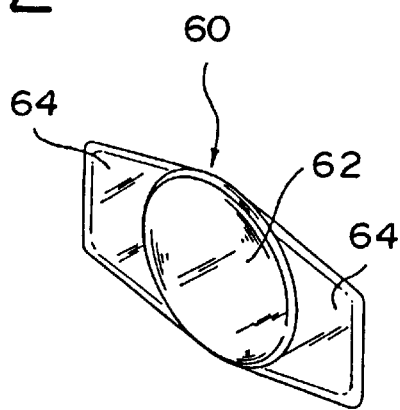
FIG. 14
FIG. 15

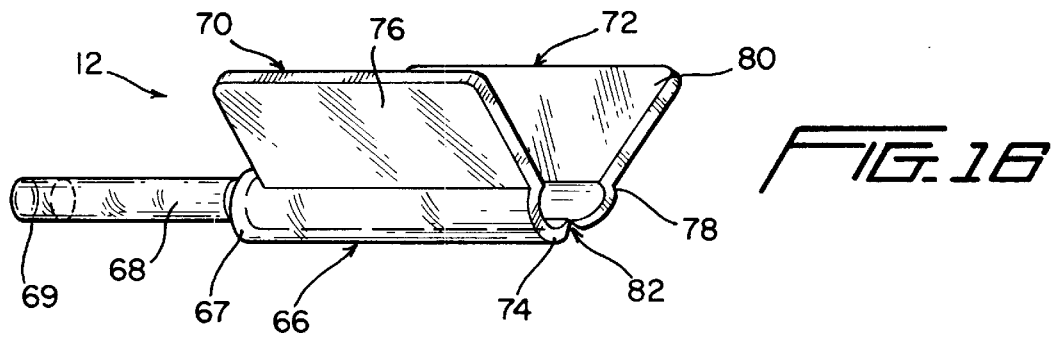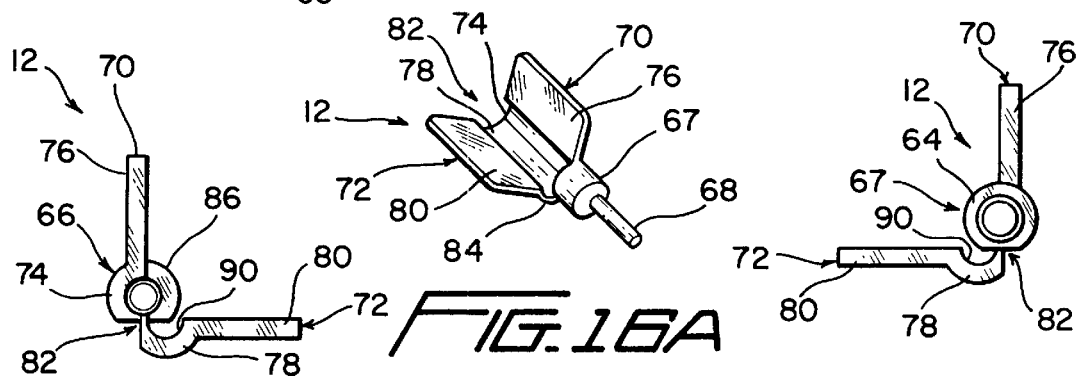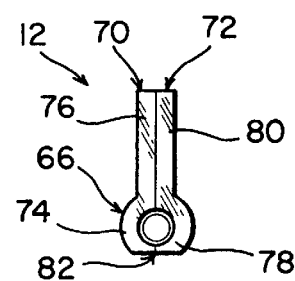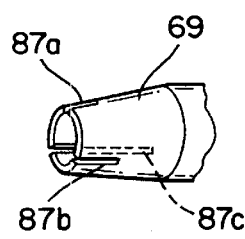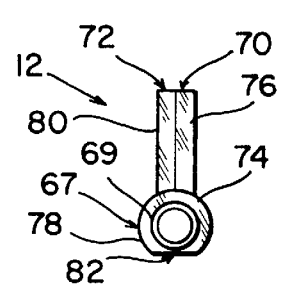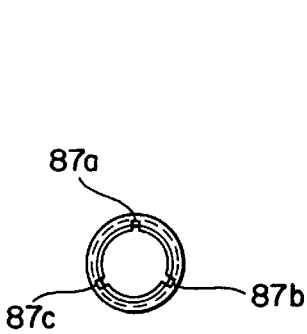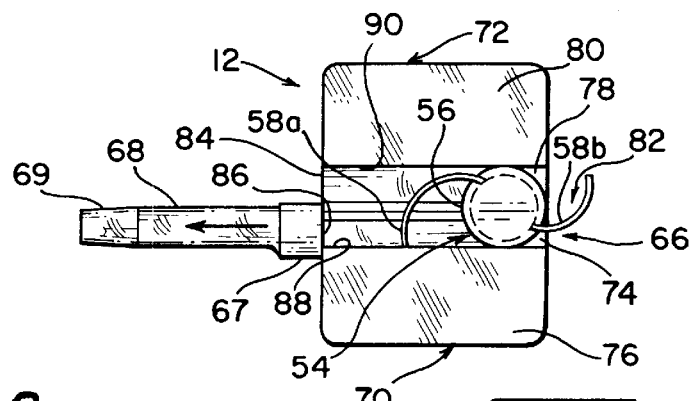

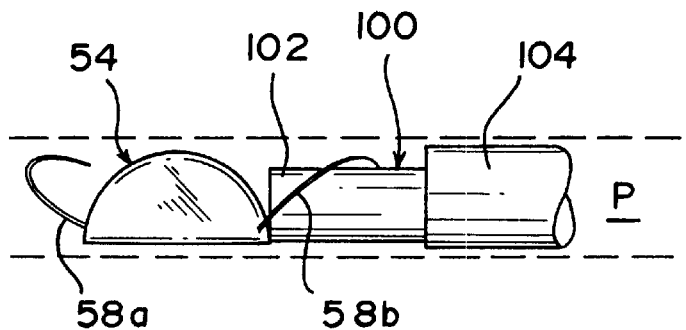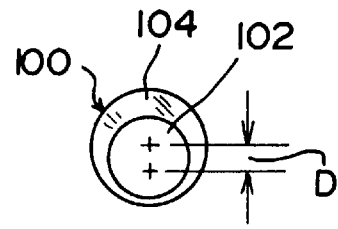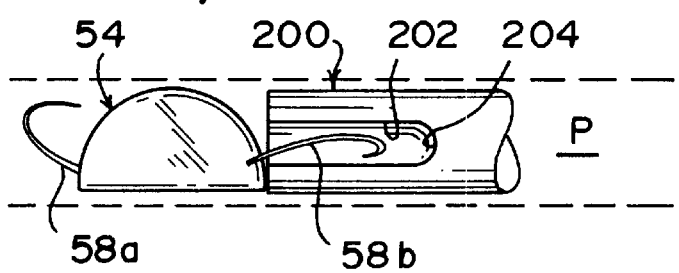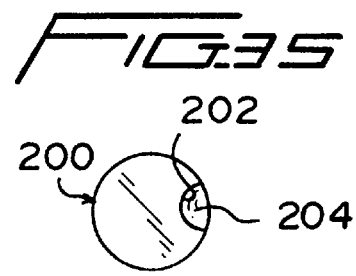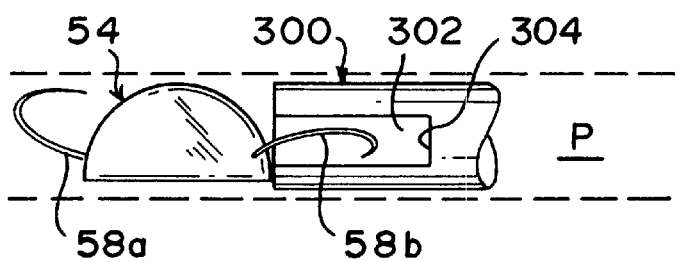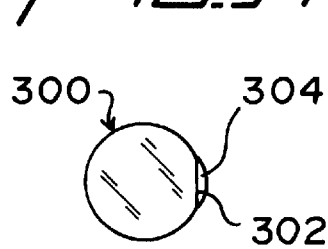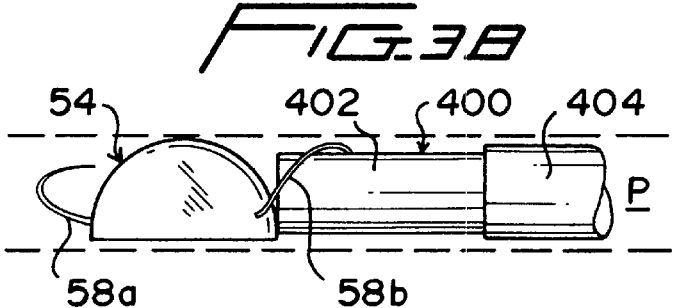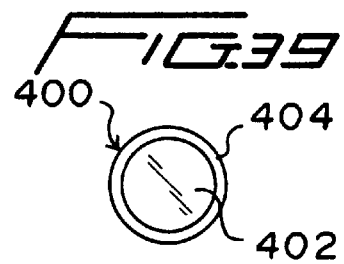

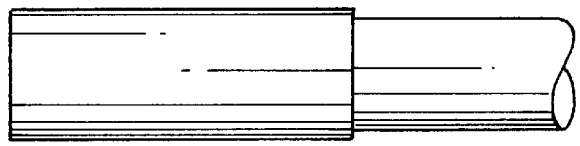
FIG. 42
PRIOR ART
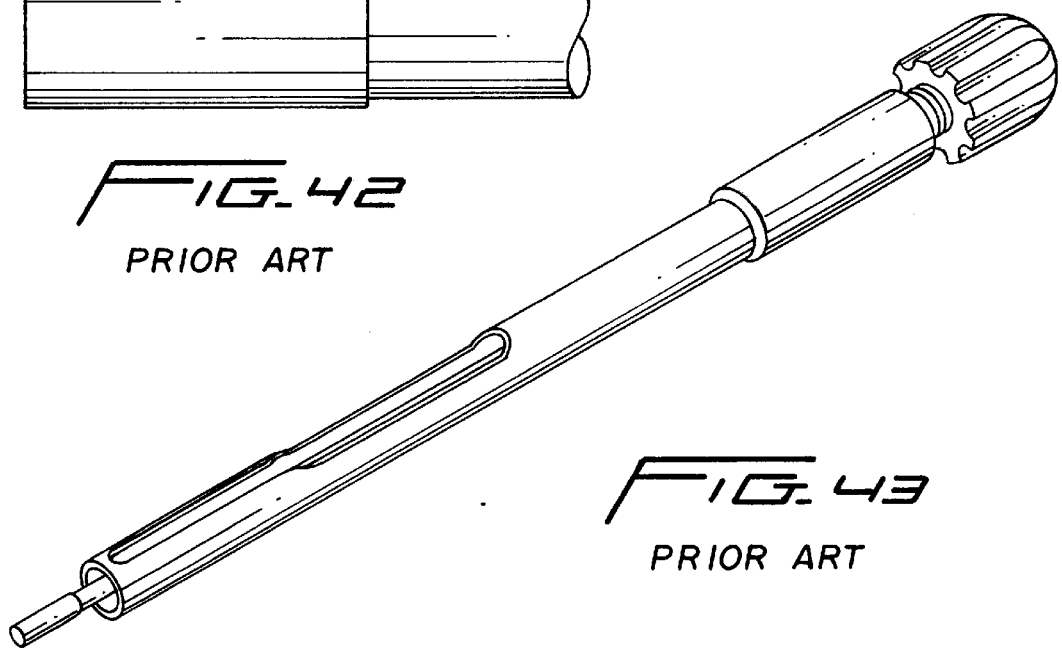
FIG. 43
PRIOR ART
FIG. 44
PRIOR ART
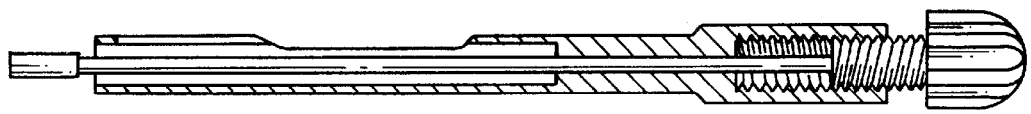
FIG. 45
PRIOR ART
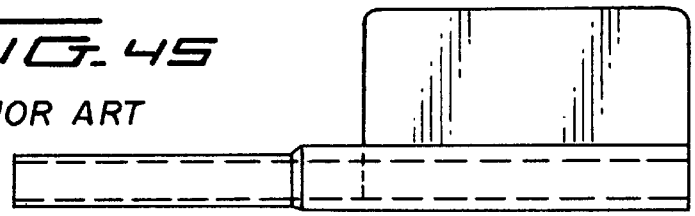
FIG. 46
PRIOR ART
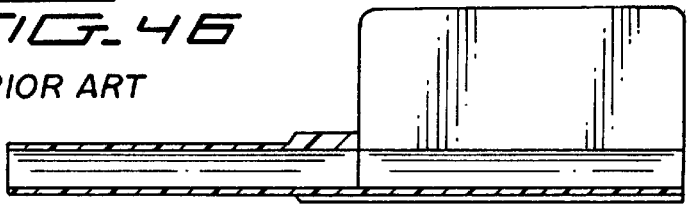

DEFORMABLE INTRAOCULAR LENS INJECTING DEVICE

RELATED APPLICATIONS

This is a divisional of U.S. patent application entitled: "DEFORMABLE INTRAOCULAR LENS INJECTING DEVICE," Ser. No. 08/403,530, filed on Mar. 14, 1995, now abandoned, which is a continuation-in-part of U.S. patent application entitled "DEFORMABLE INTRAOCULAR LENS INSERTION SYSTEM", Ser. No. 08/221,013, filed on Apr. 1, 1994, issued as U.S. Pat. No. 5,494,484 on Feb. 27, 1996, which is a continuation of U.S. patent application entitled "INTRAOCULAR LENS INSERTION SYSTEM", Ser. No. 07/953,251, filed on Sep. 30, 1992, now abandoned, both applications fully incorporated by reference herein.

FIELD OF THE INVENTION

This invention relates to a deformable intraocular lens injecting device for use with a lens cartridge. Specifically, the present invention is directed to the tip structure of a plunger of the deformable intraocular lens injecting device configured to prevent damage to a trailing haptic of a deformable intraocular lens loaded in the lens cartridge, which lens cartridge is loaded into the lens injecting device.

BACKGROUND OF THE INVENTION

Staar Surgical Company of Monrovia, Calif. has been actively producing and selling deformable intraocular lens since the early 1980s. Dr. Mozzocco who affiliated with Staar Surgical Company invented and patented the first commercially successful deformable intraocular lens. Dr. Mozzocco also developed a number of methods (i.e. techniques) and devices for implantation of deformable intraocular lens.

Staar Surgical Company began distributing a deformable intraocular lens surgical implantation system in 1986, which included a device that became known as the "Staar Shooter" for use with disposable plastic lens cartridges. An example of the prior art "Staar Shooter" device is shown in FIGS. 42–46. It is important to note the plunger tip of this device was a cylindrical shaped, and had a flat circular end face, as shown in FIG. 42.

The Staar Shooter device was used by surgeons in the United States and around the world in tens of thousands of deformable intraocular lens implantation surgical procedures. Even though the "Staar Shooter" device performed very well and was highly accepted and used by practicing surgeons, the device could potentially be improperly operated. For example, in a small number of incidences, the trailing haptic of the deformable intraocular lens was damaged by being caught between the plunger tip and inner wall of the passageway through the lens cartridge during insertion. Specifically, there existed a small clearance between the outer diameter of the plunger tip and the inner wall of the passageway through the lens cartridge allowing the trailing haptic to potentially enter into a void space created by the small clearance, and then become wedged and further wedged as the plunger tip was forced through the passageway in the lens cartridge. The forces due to this wedging action were significant in some cases to cause permanent deformation of the trailing haptic due to tensile and shear stress applied to the trailing haptic.

Another potential for damage to the trailing haptic could occur with the "Staar Shooter", if the deformable intraocular lens was improperly loaded into the lens cartridge. Specifically, the entire deformable intraocular lens including the trailing haptic needed to be loaded into the lens cartridge prior to loading the lens cartridge into the lens injecting device. A surgeon or surgical support staff personnel could potentially improperly load the deformable intraocular lens with the trailing haptic at least partially extending out of the passageway of the lens cartridge. If the deformable intraocular lens was improperly loaded in this manner, the trailing haptic could easily be damaged by the tip of the plunger of the "Staar Shooter" by being caught between the circular edge of the end face of the plunger tip and the circular edge of the opening into the passageway. If the trailing haptic became caught in this manner and further force was applied to the plunger, the circular edge of the end face of the plunger tip and the circular end of the opening in the passageway could cut into the trailing haptic potentially permanently damaging the same.

These and other situations could potentially occur resulting in permanent damage to the trailing haptic. The resulting permanent damage to the trailing haptic is costly, since the damaged deformable intraocular lens must be discarded. Further, if the physician did not realize that the trailing haptic was actually damaged during insertion, the damage deformable intraocular lens must then be retrieved from the patient's eye potentially causing eye damage and complications.

SUMMARY OF THE INVENTION

A first object of the present invention is to provide an improved deformable intraocular lens injecting device ("shooter").

A second object of the present invention is to provide an improved deformable intraocular lens injecting device comprising a plunger having a plunger tip configured to prevent damage to the trailing haptic of the deformable intraocular lens.

A third object of the present invention is to provide an improved deformable intraocular lens injecting device comprising a plunger having a plunger tip providing side clearance between the plunger tip and inner wall of the lens cartridge to accommodate the trailing haptic of the deformable intraocular lens to prevent damage thereto during insertion.

A fourth object of the present invention is to provide an improved deformable intraocular lens injecting device comprising a plunger having a plunger tip having an outer diameter sufficiently less than the inner diameter of the lens cartridge to provide a side clearance between the plunger tip and inner wall of the lens cartridge to accommodate the trailing haptic of the deformable intraocular lens to prevent damage thereto during insertion.

A fifth object of the present invention is to provide an improved deformable intraocular lens injecting device comprising a plunger having a plunger tip provided with a side groove to provide a side clearance between the plunger tip and inner wall of the lens cartridge to accommodate the trailing haptic of the deformable intraocular lens to prevent damage thereto during insertion.

A sixth object of the present invention is to provide an improved deformable intraocular lens injecting device comprising a plunger having a plunger tip provided with a side facet to provide a side clearance between the plunger tip and inner wall of the lens cartridge to accommodate the trailing haptic of the deformable intraocular lens to prevent damage thereto during insertion.

The present invention is direct to improved deformable intraocular lens injecting devices having specially designed plunger tip configurations each providing a side clearance between the plunger tip and inner wall of the lens cartridge to accommodate the trailing haptic of the deformable intraocular lens to prevent damage thereto during insertion.

The side clearance allows the end of the plunger tip to be placed in direct contact with the deformable intraocular lens when loaded in the lens cartridge without contacting or contacting the trailing haptic of the deformable intraocular lens in a manner that could potentially damage the same during insertion.

The side clearance between the plunger tip and inner wall of the passageway through the lens cartridge allows the trailing haptic to be received or accommodated in the void space created by the side clearance in a manner that the trailing haptic is not subject to tensile or shear stresses during the insertion mode. Specifically, the trailing haptic is accommodated so that it cannot be caught between the plunger tip and inner wall of the passageway through the lens cartridge that could potentially compress the trailing haptic by wedge action, twist the trailing haptic causing shear stresses inside the trailing haptic resulting in substantial strain and potential permanently deformation by exceeding the elastic limits of the material used to make the trailing haptic. Further, the side clearance is preferable made to enclosed or captivate the trailing haptic to maintaining the trailing haptic in a certain configuration and again protect it during insertion.

A method according to the present invention includes lubricating the surface of a deformable intraocular lens with a surgically compatible lubricant, and loading the deformable intraocular lens into a lens cartridge in the opened position. The lens cartridge is closed while condensing the deformable intraocular lens by a folding action into a shape so that it can be forced through the passageway in the cartridge. The lens cartridge is inserted into the lens injecting device with the plunger retracted.

The plunger is moved forward in a sliding manner by pushing the plunger forward while holding the lens cartridge still. This action forces the deformable intraocular lens from the lens holding portion of the lens cartridge into the nozzle portion. At this point the threads of the threaded end cap of the plunger engage with the threads of the threaded sleeve. The threaded end cap is rotate slightly to engage the threads. The device is now ready for the implantation process.

The nozzle portion of the lens cartridge is placed through a small incision in the eye. The threaded end cap of the plunger is rotated or dialed to further advance the deformable intraocular lens forward through the nozzle portion and into the eye. The threaded end cap is further dialed to exposed the tip of the plunger within the eye and push the deformable intraocular lens into position. The tip can be used to also rotate the lens within the eye for positioning of the haptics.

BRIEF DESCRIPTION OF THE DRAWINGS

FIG. 1 is a perspective view of one embodiment of the surgical implantation device according to the present invention with a lens cartridge positioned in the lens injecting device for implantation of deformable lens structures for placement in the eye.

FIG. 2 is a perspective view of the surgical implantation device shown in FIG. 1 with the plunger retracted, and with the lens cartridge removed.

FIG. 3 is a side view of the surgical implantation device shown in FIG. 2 with the plunger in the extended position.

FIG. 4 is a side elevational view of the surgical implantation device shown in FIG. 1.

FIG. 5 is a detailed longitudinal cross-sectional view of the surgical implantation device shown in FIG. 4.

FIG. 6 is a detailed transverse cross-sectional view of the surgical implantation device, as indicated in FIG. 5.

FIG. 7 is a detailed end view of the surgical implantation device, as indicated in FIG. 5.

FIG. 8 is an enlarged detailed left side elevational view of the tip of the plunger in the spacial orientation as shown in FIG. 1.

FIG. 9 is an enlarged detailed end view of the tip shown in FIG. 8.

FIG. 10 is an enlarged detailed top planar view of the tip of the plunger.

FIG. 11 is an enlarged detailed right side elevational view of the tip of the plunger in the spacial orientation, as shown in FIG. 4.

FIG. 12 is an enlarged detailed bottom view of the tip of the plunger in the spacial orientation, as shown in FIG. 1.

FIG. 13 is a perspective view of a deformable intraocular lens for use in the present invention.

FIG. 14 is a perspective view of another type of deformable intraocular lens for use in the present invention.

FIG. 15 is a side view of the lens shown in FIG. 13.

FIG. 16 is a perspective view of the lens cartridge shown in the open position to allow a deformable intraocular lens to be loaded therein.

FIG. 16A is another perspective view of the lens cartridge shown in the open position.

FIG. 17 is a rear end elevational view of the lens cartridge shown in the open position.

FIG. 18 is a front end elevational view of the lens cartridge shown in the open position.

FIG. 19 is a rear end elevational view of the lens cartridge shown in the closed position.

FIG. 20 is a front end elevational view of the lens cartridge shown in the closed position.

FIG. 20A is a detailed end view of the nozzle portion showing three (3) slots of different length equally spaced about the circumference of the tip.

FIG. 20B is a detailed perspective view of the tip showing the three (3) slots of different length.

FIG. 21 is a top planar view of the lens cartridge shown in the open position.

FIG. 34 is a detailed side elevational view of another embodiment of the plunger tip contacting with the deformable intraocular lens inside the lens injecting passageway.

FIG. 35 is a detailed end elevational view of the plunger tip shown in FIG. 34.

FIG. 36 is a detailed side elevational view of a further embodiment of the plunger tip contacting with the deformable intraocular lens inside the lens injecting passageway.

FIG. 37 is a detailed end elevational view of the plunger tip shown in FIG. 36.

FIG. 38 is a detailed side elevational view of an even further embodiment of the plunger tip contacting with the deformable intraocular lens inside the lens injecting passageway.

FIG. 39 is a detailed end elevational view of the plunger tip shown in FIG. 38.

FIG. 40 is a detailed side elevational view of another further embodiment of the plunger tip contacting with the deformable intraocular lens inside the lens injecting passageway.

FIG. 41 is a detailed end elevational view of the plunger tip shown in FIG. 40.

FIG. 42 is a detailed side elevational view of a prior art plunger tip.

FIG. 43 is a perspective view of a prior art lens injecting device.

FIG. 44 is a longitudinal side cross-sectional view of the prior art lens injecting device shown in FIG. 43.

FIG. 45 is a side elevational view of a prior art disposable plastic lens cartridge.

FIG. 46 is a longitudinal cross-sectional view of the lens cartridge shown in FIG. 45.

DETAILED DESCRIPTION OF PREFERRED EMBODIMENTS

Figures 22, 23:
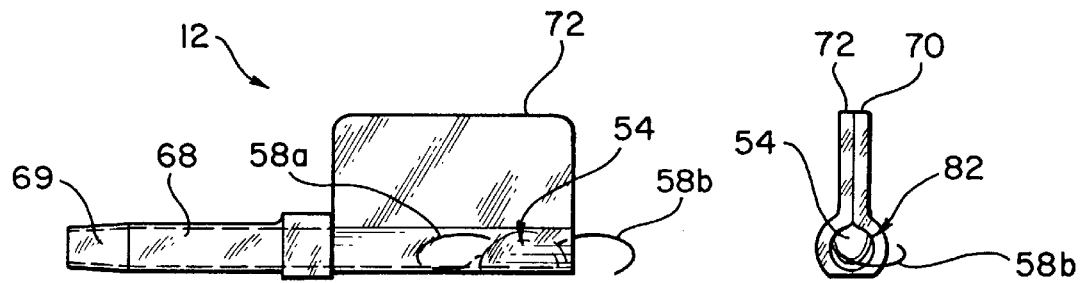
FIG. 22 is a side elevational view of the lens cartridge shown in the closed position.
FIG. 23 is a rear end elevational view of the lens cartridge shown in the closed position.

A device according to the present invention comprises a deformable intraocular lens injecting device having a plunger tip configured to provide a side clearance between the plunger tip and inner wall of a lens injecting passageway.

The present invention can be applied to the plunger tip of a separate deformable intraocular lens injecting device to be used with a separate lens cartridge (i.e. two-piece system such as disclosed herein), or can be applied to the plunger tip of an intraocular lens injecting device having a lens injecting passageway itself (i.e. one-piece system such as disclosed in U.S. Pat. No. 5,275,604 to Rheinish, fully incorporated by reference herein).

A preferred embodiment of a deformable intraocular lens surgical implantation device 10 according to the present invention is shown in FIGS. 1–3. The surgical implantation device 10 comprises a lens cartridge 12 disposed within a lens injecting device 13. The lens injecting device comprising a lens injecting body 14 with a side receiver 15, and a movable plunger 16. In FIG. 1, the side receiver 15 is defined by an opening 17 through the wall of the lens injecting body 14 of the size and shape shown in FIGS. 1 and 2. The opening 17 is defined by parallel edges 17a, 17a, which are sufficiently spaced apart to allow the lens cartridge 12 to be loaded into the side receiver 15 of the lens injecting device 13, tapered edges 17b, clamping edges 17c, and stop edge 17d. In FIG. 1, the lens cartridge 12 is positioned in the side receiver 15 between the clamping edges 17c with the plunger extending through the lens cartridge 12 in a position, for example, after a lens implantation procedure.

In FIG. 2, the lens cartridge 12 is shown removed from the lens injecting device 13 with the plunger 16 in a retracted position for allowing the lens cartridge 12 containing a loaded lens and its haptic to be inserted within the lens injecting device 13. In FIG. 3, the lens injecting device 13 is shown with the plunger 16 in the extended position without the lens cartridge 12 for purposes of illustration of the components.

The plunger 16 is fitted with a threaded end cap 18 at one end, and fitted with a tip 20 at an opposite end. The threaded end cap 18 is provided with a plurality of grooves 22 to a allow a person to tightly grip the cap 18 with his or her finger tips. The threaded end cap 18 is received within a threaded sleeve 24 of the lens injecting body 14. The threaded end cap 18 can be a separate component attached to the lens injecting device 13, or integral therewith, as shown in the construction is FIG. 5.

The plunger 16 is installed within the lens injecting device 13 in a manner to allow the plunger 16 to be reciprocated therein. In the illustrated embodiment, the plunger 16 is supported for sliding movement within the lens injecting device 13 by guide 26, as shown in FIGS. 5 and 6. The outer dimension of the guide 26 is approximately the same size as the inner dimensions of the lens injecting body 14 to allow the guide to be inserted within the lens injecting body 14. During construction, the guide 26 is inserted within the lens injecting device 13, and locked into position by pin 28 inserted into a predrilled hole in both the wall of the lens injecting device 13 and guide 26. In an alternative embodiment, the guide 26 is delete and the pin 28 is utilized to prevent rotation of the plunger 16 by the pin 28 riding along the flat side of the plunger 16, as shown in FIG. 5.

The cross-sectional shape of the plunger 16 as well as the shape of the inner surface of the guide 26 are approximately a half-circle, as shown in FIG. 6. This arrangement prevents the plunger 16 from rotating within the lens injecting device 13 to maintain the orientation of the tip 20 relative to the lens injecting device 13 during operation.

The threaded end cap 18 is connected to the plunger 16 in a manner to allow the threaded end cap 18 to be rotated relative to the plunger 16. For example, the left end of the plunger 16 (FIG. 5) is provided with a threaded extension 30, which is secured to the threaded end cap 18 by a nut 32. Specifically, the threaded end cap 18 can be made with external threads 34 and a longitudinal center bore 36 that ends on the right side of the threaded end cap 18 leaving an end wall 38.

The end wall 38 is provided with a hole slightly larger than the outer diameter of the threaded extension 30 to allow the threaded end cap 18 to freely rotate on the plunger 16 while being secured to the end of the plunger 16. During construction, the nut 32 is inserted through the center bore 36 and threaded onto the extension 30 to secure the threaded end cap 18 to the plunger 16. A curved end cap 40 is press fitted into the end of the center bore 36, and seal the center bore 36 to prevent debris from entering therein during use. Alternatively, the threaded extension 30 can be replaced with an interference type connection (e.g. snap fit type) between the modified extension and threaded end cap 18 to facilitate quick assembly.

The details of the tip arrangement are shown in FIGS. 7 to 12. The plunger 16 is manufactured with an extension 42 supporting tip 20. The tip 20 structure provides means for inserting the deformable intraocular lens into the eye and manipulating the lens within the eye after the insertion step. For example, the tip 20 is faceted in the manner shown in the figures. Specifically, the left side of the tip 20 shown in FIG. 8 is provided with a flat surface facet 44, conical surface 46, and cylindrical surface 48. The right side of the tip 20 shown in FIGS. 8 and 9 is provided with a concave surface facet 47 50, conical surface 46, and cylindrical surface 48.

The end face of the tip 20 is designed to push the lens into position once inserted into the eye. For example, the end face is defined by a 52, such as the concave cylindrical surface (e.g. cylindrical-shaped recess) shown in FIG. 8.

Suitable deformable intraocular lens for use in the present invention are shown in FIGS. 13–15. The deformable intraocular lens 54 shown in FIGS. 13 and 15 includes a lens body 56 with attachment means defined by a pair of haptics 58 each having one end anchored in the lens portion 56 and a free end for attachment to the eye tissue. The deformable intraocular lens 60 shown in FIG. 14 includes a lens body 62 and attachment means defined by a pair of lateral lobes 64 of the lens portion 62.

The details of the preferred lens cartridge 12 are shown in FIGS. 16–20. The lens cartridge 12 comprises a lens holding portion 66 extending to a transition portion 67 and an implantation nozzle portion 68. When the lens cartridge 12 is in a closed position, a continuous circular or oval passageway of the same diameter extends through the lens holding portion 66 through the transition portion 67 and through the implantation nozzle portion 68. The lens cartridge 12 is preferably made of injection molded plastic such as polypropylene. The lens holding portion 66 is defined by a fixed portion 70 and a movable portion 72. The fixed portion 70 is fixed relative to the implantation nozzle portion 68, and is defined by a tubular portion 74 and extension 76. The movable portion 72 is movable relative to the fixed portion 70 for opening and closing the lens holding portion. The movable portion 72 is defined by a tubular portion 78 and extension 80. A hinge 82 is provided between the fixed portion 70 and movable portion 72. The hinge 82 is defined by reducing the thickness of the walls of the tubular-portions; and 74 and 78 at the hinge 82, as shown in FIGS. 17, 18 and 19. The hinge 82 runs the length of the lens holding portion 66 to allow the extensions 76 and 80 to be split apart, or brought together to open and close, respectively, the lens holding portion 66.

The tubular portion 78 of the movable portion 72 is provided with a sealing edge 84, which is exposed when the lens cartridge 12 is opened, as shown in FIG. 16A, and seals with a similar sealing edge 86 (See FIG. 17) of the transition portion 67 when the lens cartridge 12 is closed.

The end of the nozzle tip 69 is provided with three (3) equally spaced slots 87a, 87b and 87c of different length provided about the circumference thereof, as shown in FIGS. 20A and 20B. The slot 87a positioned at the top of the nozzle tip 69 is the shortest, slot 87c on the right side of the nozzle tip 69 is the longest, and slot 87b on the left side is of medium length. The slots 87a, 87b, 87c cause the lens 54 to rotate as it exits the nozzle tip 69.

Other embodiments of the lens cartridge 12 according to the present invention are shown in FIGS. 30–33.

Figure 30:
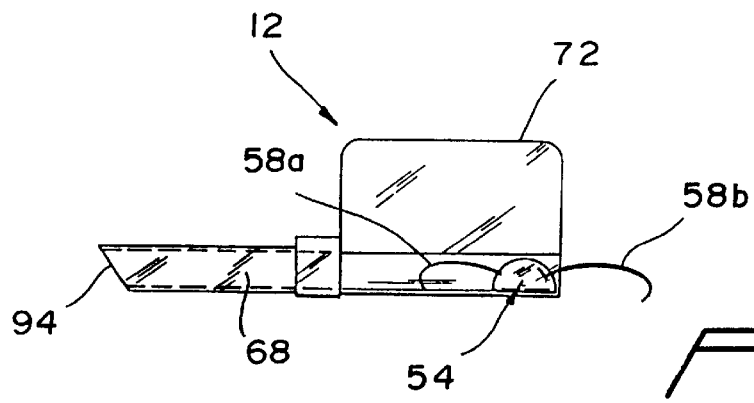
FIG. 30 is a side elevational view of an alternative embodiment of the lens cartridge provided with a beveled tip.

The lens cartridge 12 shown in FIG. 30 is provided with a beveled tip 94 to facilitate entry of the tip through the incision in the eye during implantation. The beveled tip 94 can be set at approximately forty-five (45) degrees relative to the passageway through the lens cartridge 12.

Figure 31:
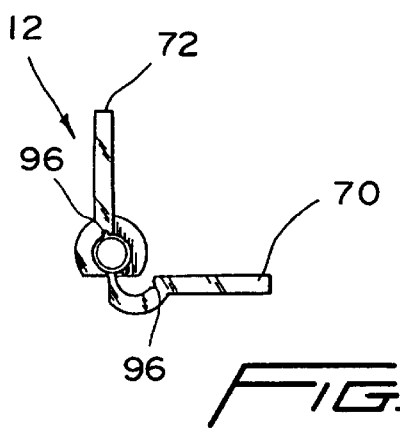
FIG. 31 is a rear end elevational view of another alternative embodiment of the lens cartridge provided with grooves in the passageway to facilitate folding the deformable intraocular lens in an open position.
Figure 32:
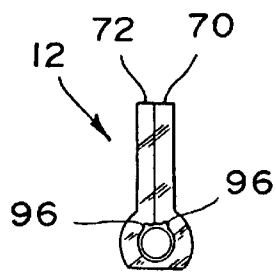
FIG. 32 is a rear end elevational view of another alternative embodiment of the lens cartridge provided with grooves in the passageway to facilitate folding the deformable intraocular lens in a closed position.

The embodiment of the lens cartridge 12 shown in FIGS. 31 and 32 is provided with a set of grooves 96 provided inside the passageway therethrough. The grooves accommodate the edges of the lens being loaded into the lens cartridge 12 to facilitate bending of the lens. Specifically, the edges of the lens are placed in the grooves 96 to prevent relative slippage of the edges with the inner surface of the passageway through the lens cartridge 12 when the lens cartridge 12 is being folded into the closed position.

Figures 33A, 33B:
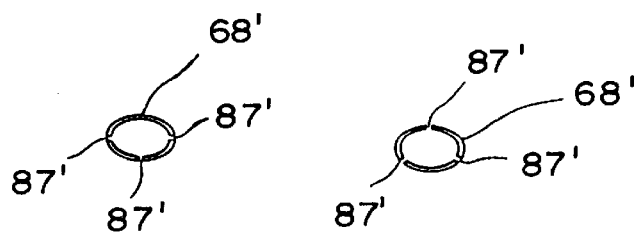
FIG. 33A is a front end elevational view of the nozzle portion of an alternative embodiment of the lens cartridge.
FIG. 33B is a front end elevational view of the nozzle portion of a further alternative embodiment of the lens cartridge.

The embodiments of the lens cartridge 12 shown in FIGS. 33A and 33B each have a nozzle portion 68' having an oval cross-section with slots 87' differently position as shown, respectively, again to facilitate entry through an incision in the eye. Alternatively, the cross-section can be two half circles set apart and connected together rather than oval.

The various features of the lens cartridges 12 shown in FIGS. 16–21 and 30–33 can be used in various combinations to achieved an optimum design for a particular application. However, all of these features are typically considered improvements of the basic combination.

The components of the device 10, except for the lens cartridge 12, are preferably fabricated from autoclavable material such as stainless steel or from a disposable rigid plastic such as medical grade ABS or the like.

ALTERNATIVE PLUNGER TIP CONFIGURATIONS

Additional embodiments of plunger tips are shown in FIGS. 34 to 41. These plunger tips all provide a side clearance between the plunger tip and lens insertion passageway to accommodate the trailing haptic.

In FIG. 34, a plunger tip 100 is shown contacting with the deformable intraocular lens 54 in the lens injecting passageway P while accommodating the trailing haptic 58b between plunger tip 100 and inner surface wall of the lens injecting passageway P.

The plunger tip 100 comprises a distal plunger tip portion 102 having a cylindrical shape and a proximal plunger tip portion 104 having a cylindrical shape, as shown in FIGS. 34 and 35. The distal plunger tip portion 102 is offset a distance D from the proximal plunger tip portion 104 to provide a larger side clearance on one side of the distal plunger tip portion 102 than on an opposite side thereof. The orientation of the offset of the distal plunger tip portion 102 relative to the proximal plunger tip portion 104 can be varied to accommodate the trailing haptic due to its location and orientation inside the lens injecting passageway P depending on the folding technique and placement technique of the deformable intraocular lens inside the lens injecting passageway P. Further, the trailing haptic can be configured so as to at least partially wrap around the distal plunger tip portion 102. The cross-sectional shapes of the distal and proximal plunger tip portions can be varied.

In FIG. 36, a plunger tip 200 is shown contacting with the deformable intraocular lens 54 in the lens injecting passageway P while accommodating the trailing haptic 58b between plunger tip 200 and inner surface wall of the lens injecting passageway P.

The plunger tip 200 comprises a side groove 202 having an end portion 204 for accommodating the trailing haptic 58b, as shown in FIGS. 36 and 37. The location of the side groove 202 around the periphery of the plunger tip 200 can be varied to accommodate the trailing haptic 58b due to its location and orientation inside the lens injecting passageway P depending on the folding technique and placement technique of the deformable intraocular lens 54 into the lens injecting passageway P.

The shape of the side groove 204 when viewing the side of the plunger tip 200 can be varied from rectangular to triangular, parallelogram shaped, curved edges, partial circular shaped and other suitable shapes. Further, the depth of the side groove 204 can be increased or decreased. In addition, the cross-sectional shape of the side groove 204 can be changed from half circle to rectangular, triangular, C-shaped, parallelogram and other suitable cross-sectional shapes.

In FIG. 38, a plunger tip 300 is shown contacting with the deformable intraocular lens 54 in the lens injecting passageway P while accommodating the trailing haptic 58b between plunger tip 300 and inner surface wall of the lens injecting passageway P.

The plunger tip 300 comprises a side facet 302 having an end portion 304 for accommodating the trailing haptic 58b, as shown in FIGS. 38 and 39. The location of the side facet 302 around the periphery of the plunger tip 300 can be varied to accommodate the trailing haptic 58b due to its location and orientation inside the lens injecting passageway P depending on the folding technique and placement technique of the deformable intraocular lens 54 into the lens injecting passageway P.

The shape of the side facet 304 when viewing the side of the plunger tip 300 can be varied from rectangular to triangular, parallelogram shaped, curved edges, partial circular and other suitable shapes. Further, the depth of the side facet 304 can be increased or decreased. In addition, the cross-sectional shape of the side facet 304 can be changed from half circle to rectangular, triangular, C-shaped, parallelogram and other suitable cross-sectional shapes. The number of facets and type of facets can also be varied depending on the requirement for the particular lens injection application.

In FIG. 40, a plunger tip 400 is shown contacting with the deformable intraocular lens 54 in the lens injecting passageway P while accommodating the trailing haptic 58b between plunger tip 400 and inner surface wall of the lens injecting passageway P.

The plunger tip 400 comprises a cylindrical distal plunger tip portion 402 concentric with a cylindrical proximal plunger tip portion 404, as shown in FIGS. 40 and 41. The location of the length of the cylindrical distal plunger tip portion 402 can be varied. Further, the cross-sectional shapes of the distal and proximal plunger tip portions can be varied.

The end faces of the plunger tips in the embodiments shown in FIGS. 34 to 41 are flat planar circular end faces. The configuration of these end faces can be varied to include one or more concave, convex, faceted, curved surface configuration and peripheral shapes depending on the particular lens injection application.

METHODS OF IMPLANTATION

The surgical procedure begins by coating the lens with a surgically compatible lubricant, and loading the lens into the lens cartridge 12. For example, as shown in FIG. 21, a lens 54 having a lens body 56, a leading haptic 58a is loaded into the lens cartridge 12 while a trailing haptic 58b remains trailing outside the lens cartridge 12 in the manner shown. Specifically, the lens 54 is loaded downwardly into the opened lens cartridge 12 until it sits on the inner surfaces of the tubular portions 74 and 78, for example, with a pair of tweezers. The outer circumferential surface edges of the lens 54 are held by edges 88 and 90 of the tubular portions 74 and 78, respectively. The rear edge of the lens 54 is placed approximately at the rear edge of the lens cartridge 12. The lens 54 is further manipulated to situate the haptics 58a and 58b in the manner shown. Specifically, haptic 54a is positioned in a leading position and the other haptic 54b is positioned in a trailing position outside the lens cartridge with respect to the direction of implantation, as indicated by the arrow.

Subsequently, the lens holding portion 66 of the lens cartridge 12 is closed about the lens 54 by forcing the extensions 76 and 80 together with his or her finger tips. The inner surfaces of the tubular portions 74 and 78 bend and fold the lens 54 when the extensions 76 and 80 are forced together, as shown in FIGS. 22 and 23. Due to the resilient nature of the deformable intraocular lens 54, the lens 54 conforms to the curved inner surfaces of the tubular portions 74 and 78 without damage thereto, as shown in FIG. 23.

The lens cartridge 12 containing the loaded lens 54 is inserted between the edges 17a, 17a of the opening 17 into the lens cartridge receiver 15 of the lens injecting device 13. As the lens cartridge 12 is moved forward, the extensions 76 and 80 move past the tapered edges 17b, 17b and come to a stop position between the clamping edges 17c, 17c when front portions of the extensions 76 and 80 contact with the stop edge 17d. The clamping edges 17c prevent rotation of the lens cartridge 12 inside the lens injecting device 13.

Figure 24:
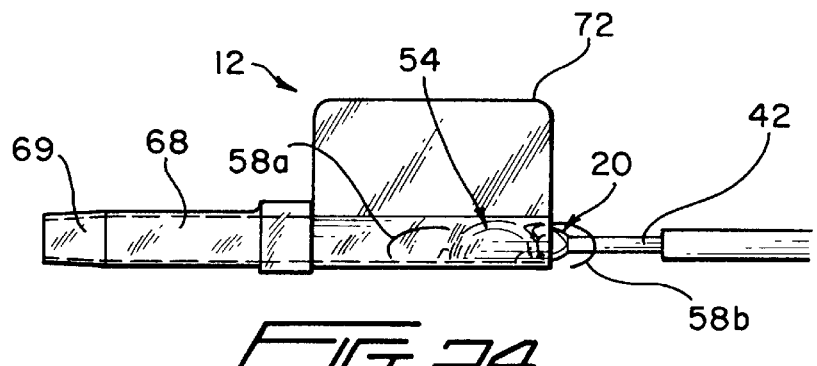
FIG. 24 is a broken away side view of the device showing the lens cartridge in relationship to the plunger in the retracted position.
Figure 25:
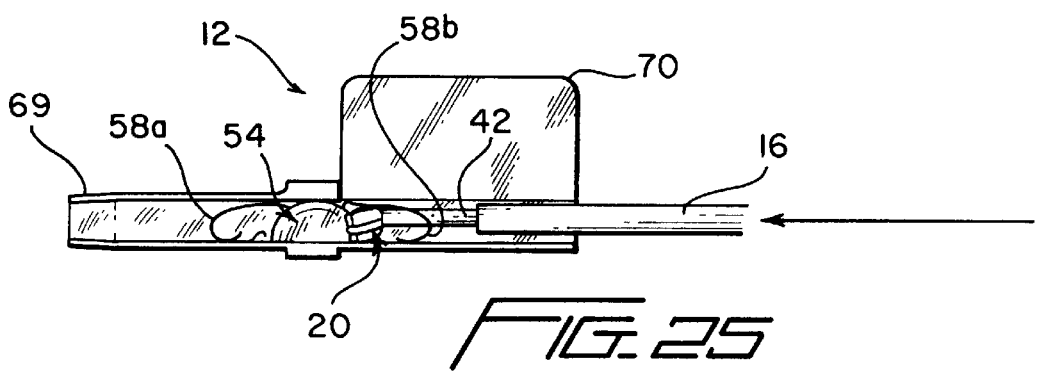
FIG. 25 is a broken away side view of the surgical implantation device showing the lens cartridge in relationship to the plunger in a partially extended position.

The user pushes the threaded end cap 18 forward while securing the lens injecting body 14 from movement, forcing the plunger 16 forward within the lens injecting device 13. As the plunger 16 is moved forward, the tip 20 enters into the rear of the lens cartridge 12 and misses the trailing haptic 58B until the tip makes contact with the loaded lens 54, as shown in FIG. 24. As the plunger 16 is moved forward in this manner, the lens 54 previously lubricated, is forced into the implantation nozzle portion 68 of the lens cartridge 12, as shown in FIG. 25.

Figure 26:
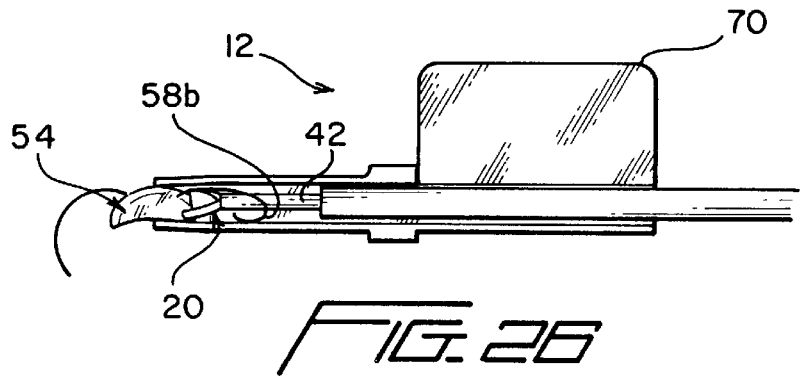
FIG. 26 is a broken away side view of the device showing the lens cartridge in relationship to the plunger in a fully extended position.
Figure 27:
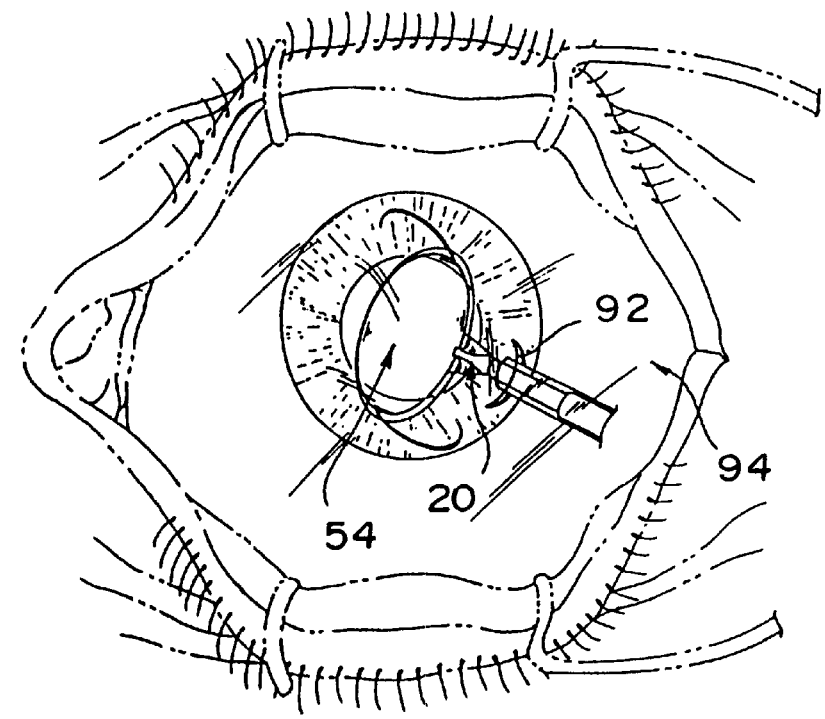
FIG. 27 is a perspective view showing the device positioning a deformable intraocular lens within the eye.

Once the deformable intraocular lens 54 enters the implantation nozzle portion 68, the threads of the end cap 18 contact with the threads of the sleeve 24 stopping further movement of the plunger 16 forward in this manner. The end cap 18 is slightly rotated to engage the threads of the end cap 18 with the threads of the sleeve 24. At this point, the surgical implantation device is ready for the implantation step. The nozzle tip 69 of the nozzle portion 68 is insert through the incision in the eye, and the end cap 18 is rotated to continue the forward movement of the plunger 16 by continued rotation of the end cap 18 relative to the lens injecting body 14 to expel the lens from the nozzle tip 69 into the interior of the eye, as shown in FIG. 26. This manner of screw advancement for moving the plunger 16 forward provides for precise control and accuracy concerning forcing the lens 54 through the remaining portion of the tip 68 into the eye during the implantation procedure. The deformed lens after exiting the nozzle portion 16 returns to its original configuration, full size and fixed focal length.

Figure 28:
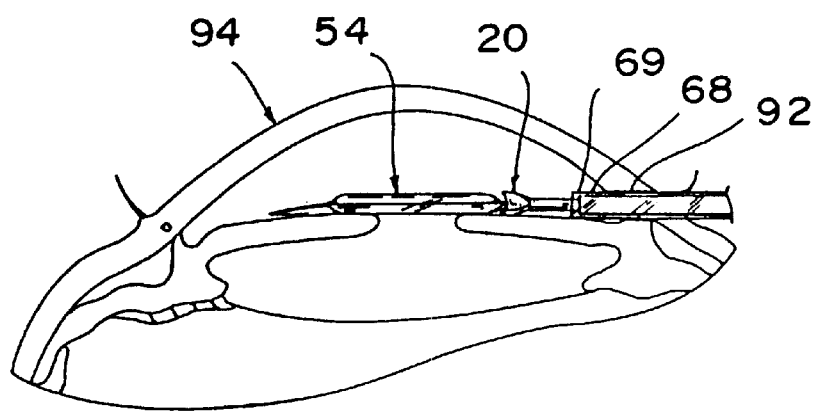
FIG. 28 is a cross-sectional view of an eye showing the positioning of the deformable intraocular lens into position in the eye by the surgical implantation device.
Figure 29:
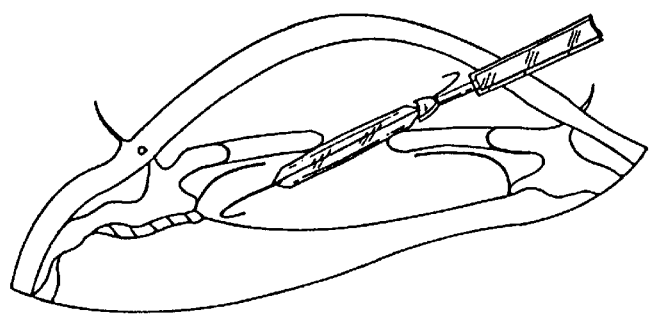
FIG. 29 is a cross-sectional view of an eye showing the positioning of the deformable intraocular lens into a different position in the eye by the surgical implantation device.

After the lens is inserted through the incision 92 into the eye, the end cap 18 is further rotated to fully expose the tip 20 of the plunger 16, as shown in FIGS. 28 and 29, to allow the lens to be pushed forward, side manipulated to rotate the lens, and pushed down to properly position the lens within the eye without the aid of other surgical instruments.

The configuration of the tip 20 is important during the implantation process. The faceted tip 20 provides a clearance between the tip 20 and the inner surface of the passageway through the lens cartridge 12 to accommodate the trailing haptic 58b during movement of the lens within the lens cartridge 12, as shown in FIGS. 25 and 26. Specifically, there exists a sufficient clearance between the flat surface facet 44 and the inner wall of the passageway through the lens cartridge 12. During the implantation process, the trailing haptic 58b floats around in the space between the extension 42 of the tip 20 and the inner wall of the passageway, as shown in FIG. 25. This prevents any chance of damage to the trailing haptic, for example, by being caught between the tip 20 and the lens 54 during the implantation process. The leading haptic 58a moves through the passageway unimpeded during the implantation process preventing any damage thereto.

We claim:

1. A deformable intraocular lens injecting apparatus for inserting a deformable intraocular lens into the eye through a relatively small incision made in the ocular tissue, said apparatus comprising:

a body portion having a nozzle portion configured for insertion through the relatively small incision made in the ocular tissue, said nozzle portion having a lens delivery passageway extending therethrough and configured to receive the deformable intraocular lens, said lens delivery passageway including at least on e groove;

a plunger having a plunger tip movably disposed in said lens delivery passageway, said plunger tip provided with a recess provided in an end face of said plunger tip for gripping an edge of said deformable intraocular lens.

2. An apparatus according to claim 1, wherein said plunger tip provided with an upper gripping edge and a lower gripping edge with said recess located therebetween.

3. An apparatus according to claim 2, wherein one of said upper gripping edge and said lower gripping edge is wider relative to the other.

4. An apparatus according to claim 1, wherein said recess is defined by a cylindrical-shaped recess.

5. An apparatus according to claim 1, wherein a plunger tip is provided with a side facet to provide a side clearance between said distal plunger tip portion and an inner wall of said lens delivery passageway to accommodate a trailing haptic of the deformable intraocular lens to prevent damage to the trailing haptic during insertion.

6. An apparatus according to claim 5, wherein said plunger tip is provided with a pair of opposed side facets.

7. An apparatus according to claim 6, wherein said pair of opposed side facets are inclined when viewing said plunger tip from an end of said distal plunger tip portion.

8. An apparatus according to claim 1, wherein said apparatus is defined by a lens injecting device having a lens cartridge receiver and a lens cartridge.

9. An apparatus according to claim 8, wherein said lens cartridge includes a lens holding portion connected to a nozzle portion.

10. An apparatus according to claim 1, wherein said lens delivery passageway is provided with a pair of opposed grooves.

11. An apparatus according to claim 1, wherein said lens delivery passageway includes an inwardly tapering portion.

12. The apparatus of claim 1, wherein the plunger tip is configured for providing a side clearance between said plunger tip and an inner wall of the lens delivery passageway to accommodate a trailing haptic of the deformable intraocular lens without damage thereto during insertion.

13. The apparatus of claim 12, wherein said plunger tip comprises an outer diameter substantially less than the inner diameter of the lens delivery passageway to provide a void space of sufficient dimensions due to the side clearance to accommodate the trailing haptic of the deformable intraocular lens.

14. The apparatus of claim 12, wherein a distal end of said plunger tip comprises an outer diameter less than an outer diameter of a proximal end of said plunger tip.

15. The apparatus of claim 14, wherein said distal end of said plunger tip is offset from said proximal end of said plunger tip.

16. The apparatus of claim 12, wherein said plunger tip is provided with a side groove for accommodating the trailing haptic of the deformable intraocular lens.

* * * * *